(12) United States Patent
Brar et al.

(10) Patent No.: US 11,617,855 B2
(45) Date of Patent: Apr. 4, 2023

(54) SELF-WASHING CATHETER

(71) Applicants: Harjeet Brar, Bakersfield, CA (US);
Ishaan Brar, Bakersfield, CA (US)

(72) Inventors: Harjeet Brar, Bakersfield, CA (US);
Ishaan Brar, Bakersfield, CA (US)

( * ) Notice: Subject to any disclaimer, the term of this patent is extended or adjusted under 35 U.S.C. 154(b) by 707 days.

(21) Appl. No.: 16/409,802

(22) Filed: May 11, 2019

(65) Prior Publication Data
US 2020/0129731 A1 Apr. 30, 2020

Related U.S. Application Data

(60) Provisional application No. 62/697,950, filed on Jul. 13, 2018.

(51) Int. Cl.
*A61M 25/00* (2006.01)

(52) U.S. Cl.
CPC .... *A61M 25/0017* (2013.01); *A61M 25/0075* (2013.01); *A61M 2025/0056* (2013.01); *A61M 2025/0078* (2013.01); *A61M 2210/1085* (2013.01); *A61M 2210/1089* (2013.01)

(58) Field of Classification Search
CPC .......... A61M 25/0074; A61M 25/0075; A61M 2025/0076; A61M 25/0017; A61M 2025/0018; A61M 2025/0079; A61M 2025/0036; A61M 2025/105; A61M 2210/1085; A61M 2210/1089
See application file for complete search history.

(56) References Cited

U.S. PATENT DOCUMENTS

| | | | | |
|---|---|---|---|---|
| 4,227,533 A | * | 10/1980 | Godfrey | A61M 25/0075 604/266 |
| 4,579,554 A | * | 4/1986 | Glassman | A61M 25/0017 604/103.08 |
| 4,850,982 A | * | 7/1989 | Erlich | A61M 25/0111 604/103.05 |
| 5,004,455 A | * | 4/1991 | Greenwood | A61M 25/0043 604/523 |
| 5,336,178 A | * | 8/1994 | Kaplan | A61M 29/02 604/913 |
| 5,360,403 A | * | 11/1994 | Mische | A61M 25/10 604/101.02 |
| 5,460,610 A | * | 10/1995 | Don Michael | A61M 25/0133 604/101.03 |

(Continued)

*Primary Examiner* — Adam Marcetich
(74) *Attorney, Agent, or Firm* — Gary L. Eastman, Esq.; Eastman IP (57) ABSTRACT

The present invention is a self-cleaning catheter designed to impede the development of biofilm within the catheter and provide a mechanism for removing biofilm within the catheter during use by a patient. The self-cleaning catheter includes an outer shell enclosing a urine lumen. The urine lumen has the ability to be opened and closed with a urine lumen closure device and is formed with a plurality of micro ports and a plurality of macro wash ports. At least one antimicrobial lumen is affixed to the exterior of and in fluid communication with the urine lumen at the plurality of micro ports. Similarly, at least one wash lumen is affixed to the exterior of and in fluid communication with the urine lumen at the plurality of macro wash ports. Antimicrobial solutions and wash solutions are introduced into the urine lumen by the antimicrobial lumen and wash lumen respectively, even during use.

12 Claims, 9 Drawing Sheets

(56) References Cited

U.S. PATENT DOCUMENTS

| | | | |
|---|---|---|---|
| 6,167,886 B1* | 1/2001 | Engel | A61F 2/0027 |
| | | | 128/885 |
| 2004/0044307 A1* | 3/2004 | Richardson | A61M 25/0017 |
| | | | 604/102.01 |
| 2008/0188802 A1* | 8/2008 | Shah | A61M 25/1036 |
| | | | 604/523 |
| 2010/0198139 A1* | 8/2010 | Glickman | A61M 25/0017 |
| | | | 604/30 |
| 2011/0034865 A1* | 2/2011 | Wallace | A61M 3/022 |
| | | | 604/35 |
| 2012/0157969 A1* | 6/2012 | Martin | A61M 25/06 |
| | | | 604/523 |
| 2015/0045746 A1* | 2/2015 | Macy, Jr. | A61M 39/1011 |
| | | | 604/246 |
| 2016/0030708 A1* | 2/2016 | Casiello | A61M 25/0023 |
| | | | 604/218 |
| 2016/0243332 A1* | 8/2016 | Portela | A61M 25/0017 |
| 2019/0091462 A1* | 3/2019 | Bihlmaier | A61M 39/00 |
| 2020/0001045 A1* | 1/2020 | McIntyre | A61M 25/0017 |

* cited by examiner

SELF-WASHING CATHETER

CROSS REFERENCE TO RELATED APPLICATIONS

This application claims priority to U.S. provisional patent application Ser. No. 62/697,950, filed Jul. 13, 2018, which application is incorporated herein in its entirety by the reference thereto.

BACKGROUND

Catheter associated urinary tract infections are a serious issue in the medical industry. Approximately 75 percent of the urinary tract infections acquired in the hospital are associated with a urinary catheter. Moreover, urinary tract infections account for more than 30 percent of all hospital infections. Although statistics vary, a conservative estimate is more than 13,000 deaths per year resulting from catheter associated urinary tract infections.

Even when not fatal, catheter associated urinary tract infections lead to an increased risk of a variety of complications for patients and further lead to increased costs of medical treatment and great discomfort to the affected patients.

Although there are a variety of causes of catheter associated urinary tract infections, a common cause is microbes that colonize the interior surface of the urine drainage lumen in the form of a biofilm. Biofilms form when bacteria adhere to surfaces in aqueous environments and are extremely common. Many different bacterial species form biofilms and current scientific literature suggests biofilms to be complex structurally, heterogeneous and analogous to multicellular organisms. Indwelling urethral catheters will inevitably become colonized with microorganisms. This is in part because of the composition of urine itself and also in part because of materials produced in the bladder as a result of the presence of a foreign body (the catheter) in the bladder. However, the inevitable development of the biofilm is accelerated by the pooling of urine within the catheter itself as patients are often bedridden for significant periods of time. Biofilms can develop in a catheter in less than 2 days and are highly problematic for patients requiring chronic catheterization and/or patients that are relatively immobile.

Once established, biofilms are difficult to remove from a catheter. Biofilms form in layers, with the bottom layer acting as the bond to the interior of the catheter. Conventional efforts to remove the biofilm are often unsuccessful because the wash liquid rarely can penetrate the top layers of the biofilm sufficiently to affect the bonded bottom layer. For this reason, biofilms generally are resistant to removal from simple shear forces resulting from conventional washing approaches. Similarly, biofilms are also often resistant to antimicrobial agent treatments. This resistance to antimicrobial agents also result from the layering found in biofilms coupled with their heterogeneous nature. Since the antimicrobial agents are typically limited to act on the surface layer of the biofilm, the antimicrobial agents are incapable of reaching the bottom bonded layer of the biofilm thereby allowing any damaged cells of the upper layer of the biofilm to simply and quickly regrow.

Although strong biocides are regularly used for biofilm removal in water treatment industries, such biocides cannot be used safely in connection with catheters because of the potential for passage of such biocides into the bladder of the patient. As a result, conventional art does not provide a practical method of allowing wash solutions or antimicrobial agents to reach the problematic bonded bottom layer of a biofilm. In short, there is no proven method of preventing or removing biofilms in catheters during use. Currently, the best practice to minimize risk of catheter associated urinary tract infections involves merely limiting the duration of use of a catheter. However, this practice is uncomfortable to patients and increases medical costs primarily due to the extra effort required to monitor the time of usage of a catheter. Moreover, notwithstanding efforts to track catheter use duration, catheters often remain in use long enough to develop a biofilm and thereby increase risk of urinary tract infection. Even when efforts to tract duration of catheter use are performed using software, such efforts still require human effort to properly and accurately input beginning of catheter use as well as human effort to timely remove the catheter when prompted to do so. Such human involvement coupled with the rapid rate upon which a biofilm can develop ensures that catheter associated urinary tract infections will continue to be a problem, particularly in hospitals where medical providers have extreme demands for their attention and focus.

In light of the above, there is a need for a self-cleaning catheter that extends the duration of catheter use while minimizing the build-up of a biofilm within the catheter in order to decrease medical costs, increase patient comfort, and minimize risk of catheter associated urinary tract infection. There is a further need for a self-cleaning catheter which has the ability to safely remove a biofilm while the catheter remains imbedded in a patient. More specifically, there is a need to enable antimicrobial agents and wash solutions to reach the bottom layer of the biofilm during use of the catheter without increasing risk of cross-contamination to the patient. In addition, there is a need for the ability to agitate urine within the catheter to minimize instances of urine pooling within the catheter. There is a further need for automation of the catheter biofilm removal process to minimize human involvement and the likelihood of human error.

SUMMARY OF THE INVENTION

The present invention is directed to a self-cleaning catheter that satisfies the need to extend duration of catheter use while minimizing the build-up of a biofilm within the catheter during use. The self-cleaning catheter includes an outer shell with an insertion tip opposite an open end. The outer shell and insertion tip are generally dimensioned similar to conventional bladder catheters. An anchor balloon is affixed to the exterior of the outer shell adjacent the insertion tip. An anchor balloon fill port is connected to the anchor balloon and an air supply so as to allow for the inflation of the anchor balloon once the self-cleaning catheter is in place inside the bladder of the patient. Once inflated, the anchor balloon secures the insertion tip within the bladder of the patient throughout the use of the self-cleaning catheter.

The insertion tip is formed with a catheter opening connected to a urine lumen and is housed within the outer shell. The urine lumen terminates in a urine lumen connection port at the open end of the outer shell. The catheter opening is sized to receive urine from the bladder of a patient to the urine lumen. The urine lumen connection port is configured to connect to a urine drain tube, which in turn is connected to a urine storage reservoir. The urine lumen is formed with a plurality of micro ports and macro wash ports. The urine lumen is also equipped with a urine lumen closure device preferably located between the anchor balloon and the insertion tip. In one embodiment, the urine lumen closure device is a closure balloon that encircles the urine lumen near the insertion tip. When inflated, the closure balloon pinches the adjacent urine lumen effectively blocking the passage of urine passed the urine balloon and thereby functioning as an internal seal of the urine lumen. Once so sealed, the urine lumen may be washed utilizing novel features of the present invention. Once washed sufficiently to remove any present biofilm, the urine balloon is deflated to enable free flow of urine from the bladder into the urine lumen.

At least one antimicrobial lumen is formed on the exterior surface of the urine lumen and is in fluid communication with the interior of the urine lumen through the micro ports. The antimicrobial lumen is housed within the outer shell and terminates in an antimicrobial lumen connection port. A pressure reservoir is connected to the antimicrobial lumen connection port by way of an antimicrobial connection line. The pressure reservoir is filled with an antimicrobial agent known in the art and maintains a constant pressure greater than the pressure within the urine lumen so as to ensure a steady flow of antimicrobial agent into to the urine lumen through the micro ports. The steady flow of an antimicrobial agent acts to minimize the environment for the development of a biofilm through directly agitating any pooled urine adjacent the micro ports as well as chemically reacting with the microbes that form the initial bonding layer of the biofilm. The steady flow of the antimicrobial agent at the interior surface of the urine lumen creates a steady state condition of high bactericidal concentrations in the urine lumen which presents an inhospitable environment for the development of a biofilm on that interior surface of the urine lumen. The steady flow of antimicrobial agent further prevents the likelihood of urine pooling as the antimicrobial agent will ensure a minimal steady flow into and out of the urine lumen. Should additional antimicrobial agent be required, the pressure reservoir has fill port to facilitate an easy refill of the pressure reservoir. In an alternative embodiment of the present invention, the micro ports may be individually fitted with a non-return valve, such as one-way check valve.

At least one wash lumen is formed along the exterior surface of the urine lumen and is in fluid communication with the interior of the urine lumen through the macro ports. The wash lumen is housed within the outer shell and terminates in a wash lumen connection port. A wash reservoir is connected to the wash lumen connection port by way of a wash connection line. The wash reservoir may be filled with any wash composition known in the art and can include a wash composition specifically designed to alter the pH inside of the urine lumen in order to make the conditions inside the urine lumen even more inhospitable to biofilm development. The purpose of the wash lumen is to facilitate washing the interior of the urine lumen utilizing the wash composition which is passed into the urine lumen under pressure through the macro ports. The macro ports can be configured at an angle with respect to the urine lumen to facilitate a vortical flow within the interior of the urine lumen. The presence of the vortical flow further agitates any present biofilm increasing the likelihood that such biofilm will be dislodged from the interior surface of the urine lumen.

An alternative embodiment of the self-washing catheter is formed with a urine lumen, an antimicrobial lumen and a wash lumen all formed within a lower seal which is housed within a body of the self-washing catheter. The urine lumen, antimicrobial lumen and wash lumen open to a mixing chamber formed by the lower seal, the cylindrical wall of the body and a one-way main valve. The opposite ends of the urine lumen, antimicrobial lumen and wash lumen may be connected to various conduits and reservoirs as set forth above.

The alternative embodiment self-washing catheter is also equipped with a conventional anchor balloon affixed to the outer shell. The anchor balloon secures the self-washing catheter in a proper position in a bladder of a patient such that a catheter opening near an insertion tip of the catheter is in fluid communication with the bladder of a patient.

However, unlike the previous embodiment which sealed the urine lumen directly through either a valve or closure balloon, the alternative embodiment seals the mixing chamber from the catheter opening through use preferably, of a two valve system, which includes the one-way main valve and also a second one-way valve. The second one-way valve is positioned within the body of the self-washing catheter between the catheter opening and the one-way main valve which and acts as a redundant safety mechanism.

Any combinations of one-way valves known in the art may be utilized for the one-way main valve and the second one-way valve, however a preferred embodiment includes two dissimilar valves, such as ball valve and a cross-slit valve.

During use, a wash composition may be introduced into the mixing chamber via the wash lumen. The predetermined and selected pressure of the wash composition ensures that the one-way main valve will quickly close to preclude any wash composition from exiting the catheter into the bladder of the patient. The wash composition will then be directed to the path of least resistance through the urine lumen, thereby washing the same of any contaminants. An antimicrobial solution may be introduced into the mixing chamber from the antimicrobial lumen. A preselected pressure is maintained in the wash lumen and antimicrobial lumen to ensure that the antimicrobial agent is directed towards the urine lumen.

Both the antimicrobial agent and the wash composition flow rates and durations can be automated through simple technology known in the art.

BRIEF DESCRIPTION OF THE DRAWINGS

The nature, objects, and advantages of the present invention will become more apparent to those skilled in the art after considering the following detailed description in connection with the accompanying drawings, in which like reference numerals designate like parts throughout, and wherein.

DESCRIPTION

Figure 1A:
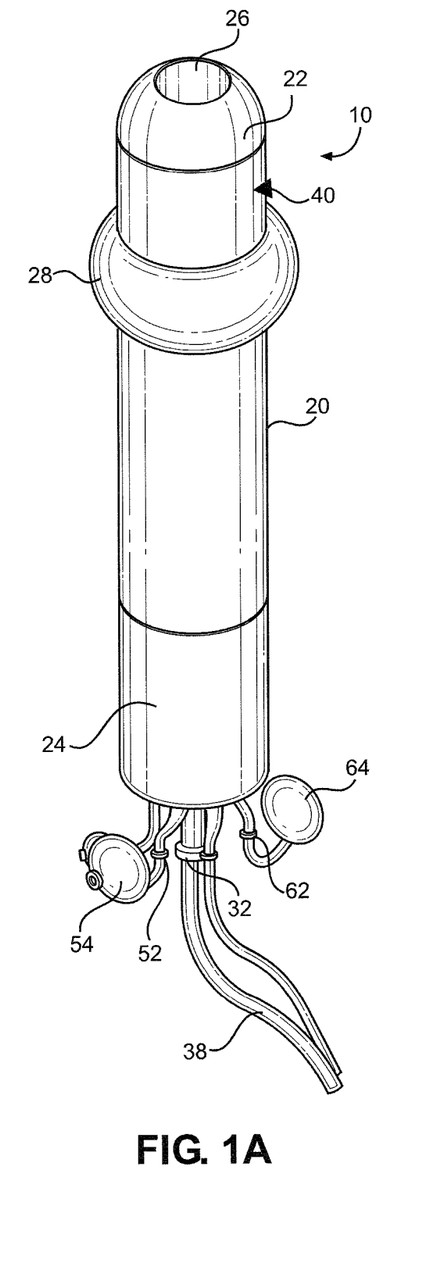
FIG. 1A is an isometric view of the self-washing catheter having a clear outer shell having an insertion tip with a catheter opening.
Figure 1B:
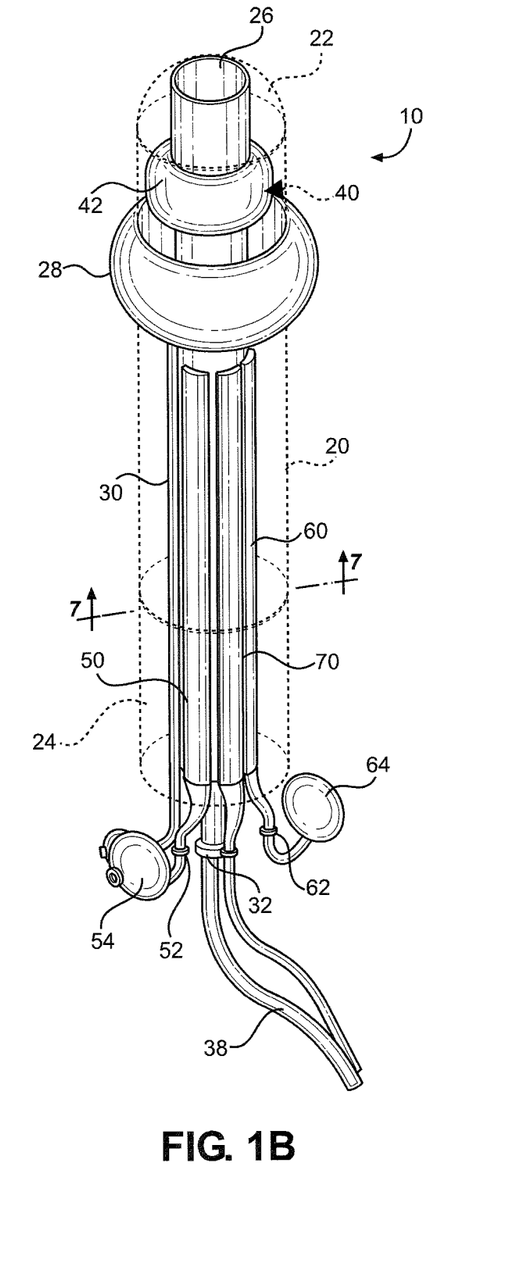
FIG. 1B is an isometric view of the self-washing catheter with the outer shell in dashed lines and showing a urine lumen connected to the catheter opening and disposed within the outer shell.

Turning to FIGS. 1A and 1B, a self-cleaning catheter 10 has an outer shell 20 with an insertion tip 22 opposite an open end 24. The outer shell 20 is shown in dashed lines in FIG. 1B to better demonstrate the internal structure of the self-cleaning catheter 10, The outer shell may be made of any conventional material known in the art, including silicone rubber, nylon, polyurethane, polyethylene terephthalate (PET), latex, and thermoplastic elastomers. Moreover, the exterior shape of the outer shell 20 and insertion tip 22 are not intended to be limiting as invention functions with any shape catheter known in the art. Also, although the specification is drawn to an embodiment for use as an indwelling urine catheter, the invention disclosed herein is equally suited for other medical catheters, as all catheters are prone to biofilm development and the potential for resulting infections.

The outer shell 20 and insertion tip 22 are generally dimensioned similar to conventional bladder catheters and may include a variety of sizes to accommodate different anatomies of patients. An anchor balloon 28 is affixed to the exterior of the outer shell adjacent the insertion tip 22. Anchor balloons 28 are known in the art and are often used in indwelling urine catheters.

Figure 3:
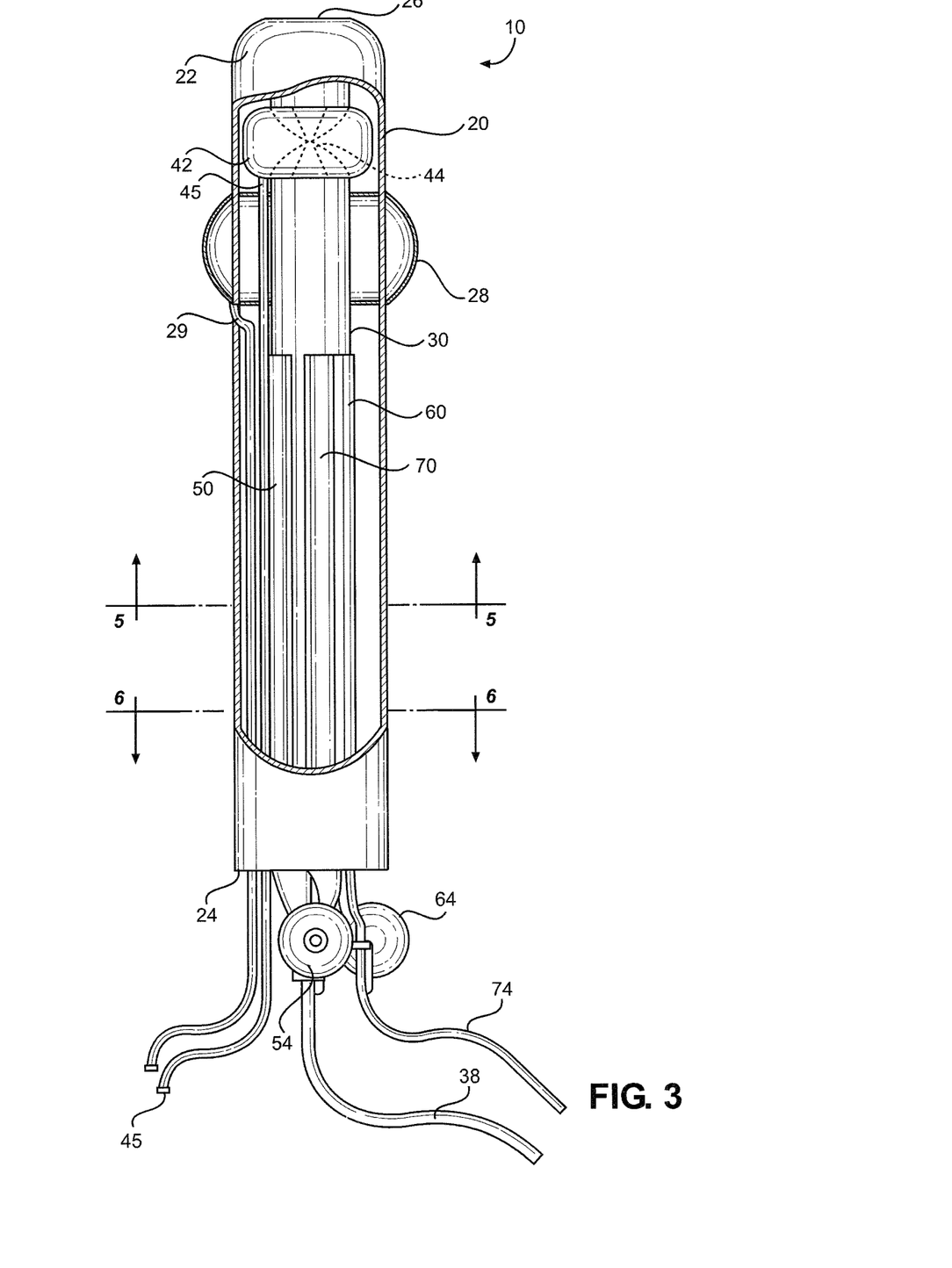
FIG. 3 is a side view of the self-washing catheter showing a urine lumen closure device in the form of a closure balloon encircling the urine lumen and the urine drain tube connecting the urine lumen to urine storage reservoir.

As can be best seen in FIG. 3, an anchor balloon fill port 29 is connected to the anchor balloon 28 and an air supply (not shown) so as to allow for the inflation of the anchor balloon 28 once the self-cleaning catheter 10 is in place inside the bladder of the patient. Once inflated, the anchor balloon 28 secures the insertion tip within the bladder of the patient throughout the use of the self-cleaning catheter. The anchor balloon fill port 29 is shown entering outer shell 20 adjacent the anchor balloon 28. Such a configuration protects the anchor balloon fill port 29 from damage during insertion of the self-cleaning catheter 10 into a patient.

Figure 6:
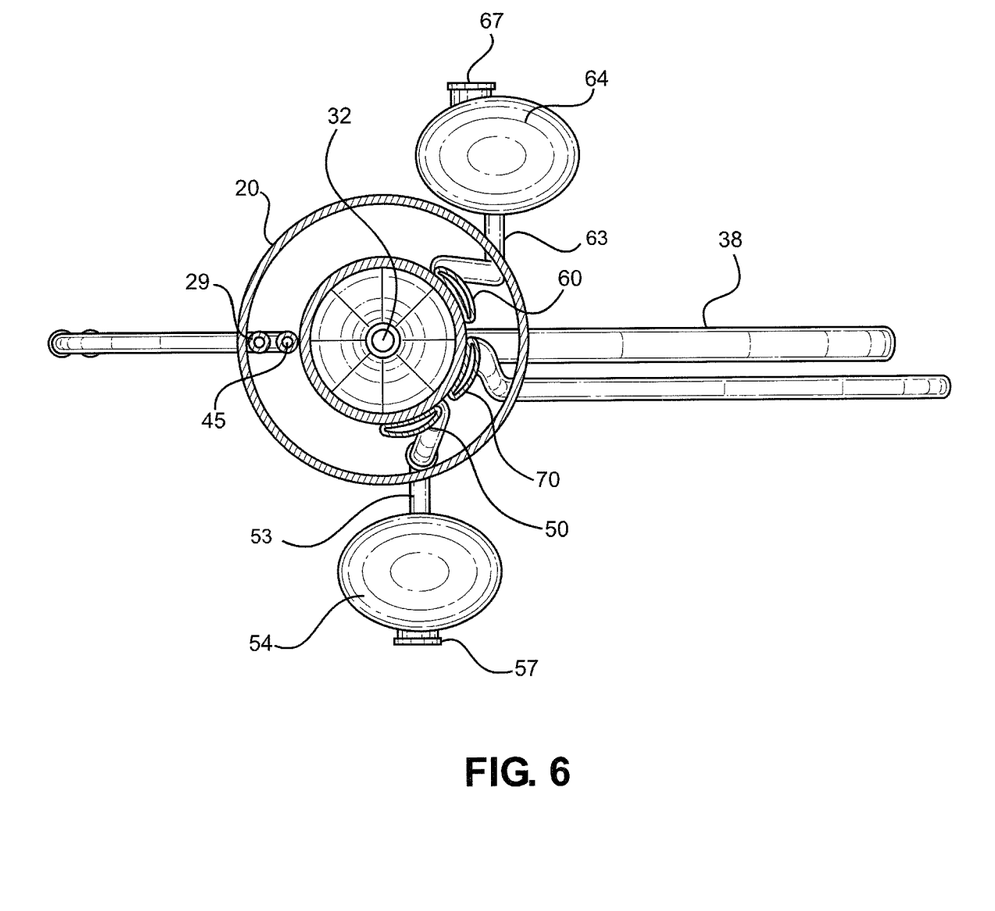
FIG. 6 is a cross-sectional view of the self-washing catheter along the lines 6-6 show in FIG. 3 and showing the cross-sectional profile of the antimicrobial lumen and the washing lumen.

Returning to FIG. 1, a catheter opening 26 formed in the insertion tip 22 serves as a point of connection to one end of a urine lumen 30. As can be best seen in FIGS. 4 and 6, the opposite end of the urine lumen 30 tapers to a urine lumen connection port 32. The urine lumen 30 has an exterior surface 31 and an interior surface 33 (shown in FIGS. 7 and 8) and is generally shown as cylindrical in shape, although this shape is not intended to be limiting. The urine lumen 30 is housed within the interior of the outer shell 20 and is accessible at the urine lumen connection port 32 near the open end 24 of the outer shell 20. An anti-biofilm coating may be applied to the interior surface 33 of the urine lumen 30.

The catheter opening 26 is sufficiently sized to easily receive urine from a bladder of a patient and direct the urine into the urine lumen 30 during normal use. The urine lumen connection port 32 serves as a quick connect to a urine drain tube 38, which in turn is connected to a conventional urine storage reservoir 14 (omitted from the Figures). During use, urine from a patient flows through the self-cleaning catheter 10 much like a conventional catheter. More specifically, urine flows from the bladder of the patient, into the catheter opening 26, through the urine lumen 30 where it is funneled into the urine lumen connection port 32, through the urine drain tube 38 and ultimately to the urine storage reservoir 14. The urine drain tube 38 and urine storage reservoir 14 are disconnected from the urine lumen connection port 32 when full allowing for a quick reconnect with a new storage reservoir.

Figure 5:
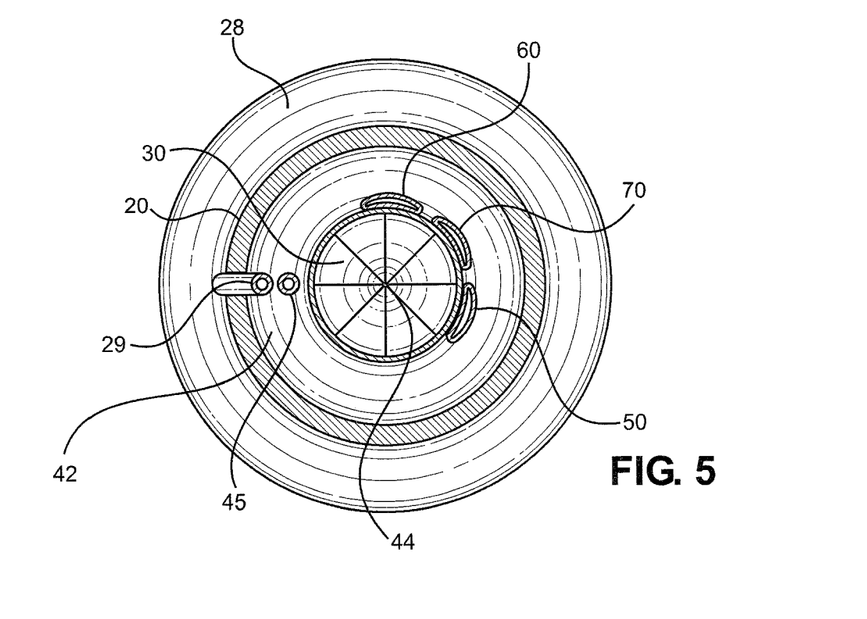
FIG. 5 is a cross-sectional view of the self-washing catheter along the lines 5-5 shown in FIG. 3 and showing the closure balloon inflated and sealing the urine lumen closed.

The urine lumen 30 has a urine lumen closure device 40 shown between the catheter opening 26 and the anchor balloon 28. As shown in FIG. 1, the urine lumen closure device 40 comprises a closure balloon 42 that encircles the urine lumen 30 near the insertion tip 22. As can be seen more clearly in connection with FIG. 5, when inflated, the closure balloon 42 pinches the adjacent urine lumen 30 sufficiently to form an internal seal 44. The closure balloon 42 is inflated via an air supply connected to closure balloon fill port 45 extending from the closure balloon 42 to adjacent the open end 24 of the outer shell 20. Once so inflated, the resulting internal seal 44 precludes the passage of urine from the bladder past the internal seal 44. Once so sealed, the urine lumen 30 may be washed as set forth more fully below to remove any biofilm or other contaminants located within the urine lumen 30. Once washed sufficiently to remove any present biofilm, the closure balloon 42 is deflated to enable free flow of urine from the bladder into the urine lumen 30.

Figure 2:
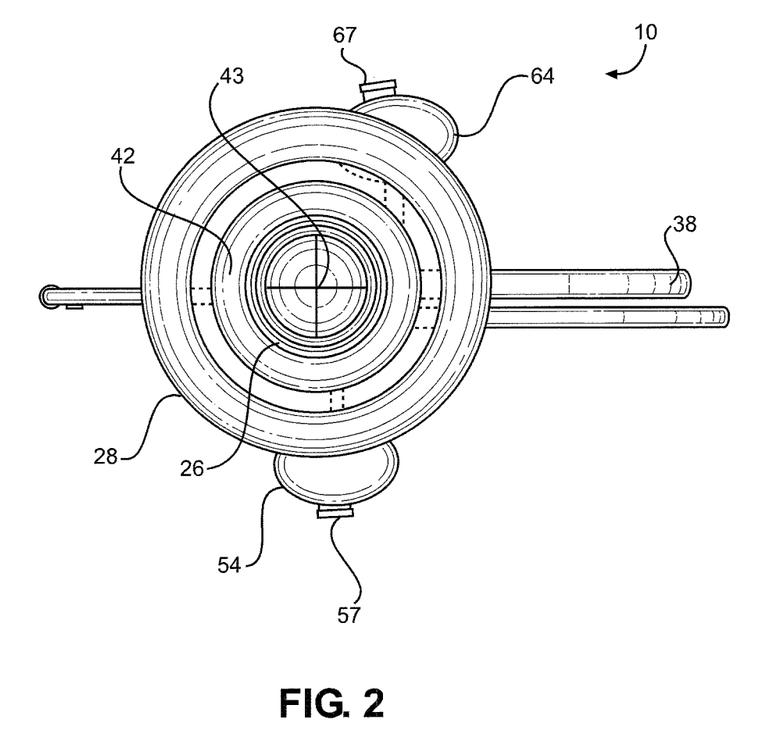
FIG. 2 shows a top view of an alternative embodiment of the self-washing catheter further showing an anchor balloon inflated along with a one-way closure valve, both cooperating together to act as a closing device.

Turning to FIG. 2, an alternative embodiment of the self-cleaning catheter 10 is shown with a one-way closure valve 43 located within the urine lumen 30 adjacent the catheter opening 26. Slight pressure of urine within the bladder will serve to open the one-way closure valve 43 which will otherwise remain closed. The one-way closure valve 43 precludes the passage of materials downstream of the one-way closure valve 43 to the catheter opening 26 and surrounding bladder. FIG. 2 also shows a closure balloon 42 as it is anticipated that the closure device 40 can include a closure balloon 42 and a one-way closure valve 43, alone or in combination.

Returning to FIG. 1b, an antimicrobial lumen 50 and a wash lumen 60 are each formed on the exterior surface 31 of the urine lumen 30. Also shown in FIG. 1b is an auxiliary lumen 70 also formed on the exterior surface 31 of the urine lumen 30. The antimicrobial lumen 50, wash lumen 60 and auxiliary lumen 70 are each in fluid communication with the interior of the urine lumen 30 and are each housed within the outer shell 20. The function of the antimicrobial lumen 50, wash lumen 60 and auxiliary lumen 70 are to introduce various compositions into the urine lumen 30 in order to impede the development of and/or remove biofilm within the urine lumen 30.

Figure 4:
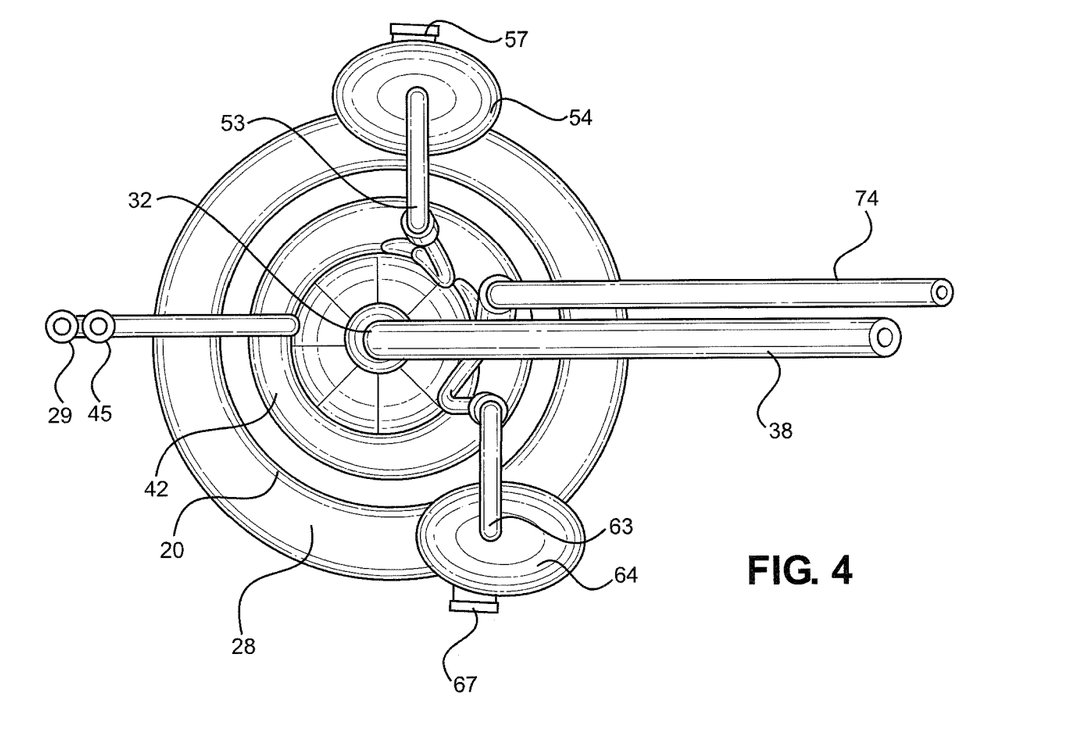
FIG. 4 is a bottom view of the self-washing catheter showing antimicrobial lumen connected to a pressure reservoir by way of a antimicrobial connection line and a wash lumen connected to a wash reservoir by way of a wash connection line.

The antimicrobial lumen 50 terminates in an antimicrobial lumen connection port 52, which in turn is connected to a pressure reservoir 54 by way of an antimicrobial connection line 53 (shown in FIG. 4). The pressure reservoir 54 holds an antimicrobial solution or agent that is driven into the urine lumen 30 by the pressure created in the pressure reservoir 54. The pressure reservoir 54 can be manually operated or automated. However, it is intended that the pressure reservoir 54 have the optional capacity to maintain a near constant pressure over a sustained period of time in order to deliver a steady dose of the antimicrobial solution or agent into the urine lumen 30 in order to act on any biofilm present therein. A primary benefit of a constant pressure is to preclude leakage from the urine lumen 30 into the antimicrobial lumen 50 during use. Another benefit of a constant pressure is to create a continual, even if small, flow of fluid through the urine lumen 30 which precludes urine pooling. The pressure reservoir 54 may be equipped with a pressure reservoir connection port 57 for connections with automated systems. Similarly, the wash reservoir 64 may be equipped with a wash reservoir connection port 57 for connections with automated systems.

The wash lumen 60 terminates in a wash lumen connection port 62, which in turn is connected to a wash reservoir 64 by way of a wash connection line 63 (show in FIG. 4). The wash reservoir 64 is used to hold a wide variety of wash compositions known in the art, from a simple saline solution to a more complex solution designed to disinfect the interior of the urine lumen 30. The wash composition can be specifically designed to alter the pH inside of the urine lumen 30 to further impede biofilm development. The purpose of the wash lumen 60 is to facilitate washing the interior of the urine lumen 30 utilizing the wash composition which is passed into the urine lumen 30 under pressure through the macro wash ports 37.

The auxiliary lumen 70 terminates in an auxiliary lumen connection port 72, which in turn is connected to an auxiliary connection line 74. The auxiliary lumen 70 can be configured as a secondary antimicrobial lumen 50, a secondary wash lumen 60, or can be used for alternative purposes such as cycling the interior of the urine lumen 30 between pressure and vacuum in order to further agitate any biofilm present within the interior surface 33 of the urine lumen 30. For such a use, the urine lumen closure device 40 would be in the closed position to preclude apply pressure or vacuum to the bladder of the patient. Numerous devices that cycle between air pressure and vacuum are known in the art and may be simply connected to the end of the auxiliary connection line 73.

Figure 7:
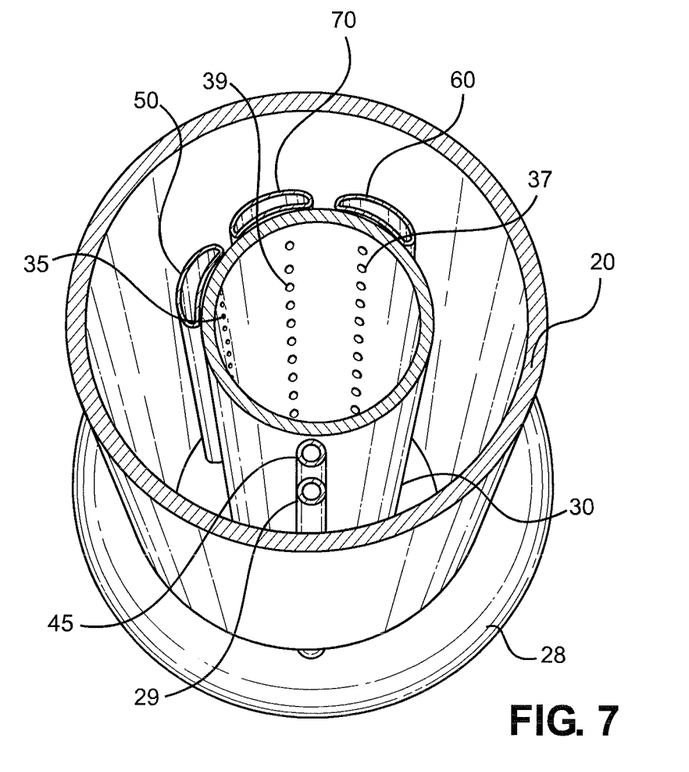
FIG. 7 is a cross-sectional isometric view of the self-washing catheter along the lines 7-7 shown in FIG. 1 and showing the micro ports and the macro ports.

As can best be seen in FIG. 7, the urine lumen 30 is formed with a plurality of micro ports 35 and a plurality of macro wash ports 37. The antimicrobial lumen 50 is positioned over the plurality of micro ports 35 so as to enable a free flow of the antimicrobial solution from the antimicrobial lumen 50 to the interior of the urine lumen 30 through the micro ports 35. Similarly, the wash lumen 60 is positioned over the plurality of macro wash ports 37 so as to enable a free flow of the wash solution from the wash lumen 60 to the interior of the urine lumen 30 through the larger macro wash ports 37. The auxiliary lumen 70 also has a plurality of auxiliary macro ports 39. The use of micro ports 35 and macro wash ports 37 enables the antibacterial agent and wash solutions to act on and near the bottom bonded layer of the biofilm to greatly increases the effectiveness of both the antibacterial agent and wash solution in removing biofilm. Further, the constant flow of antibacterial agent, even in small quantities, makes the interior surface 33 of the urine lumen 30 difficult for a developing bottom layer of a biofilm to adhere to the interior surface 33.

Figure 8:
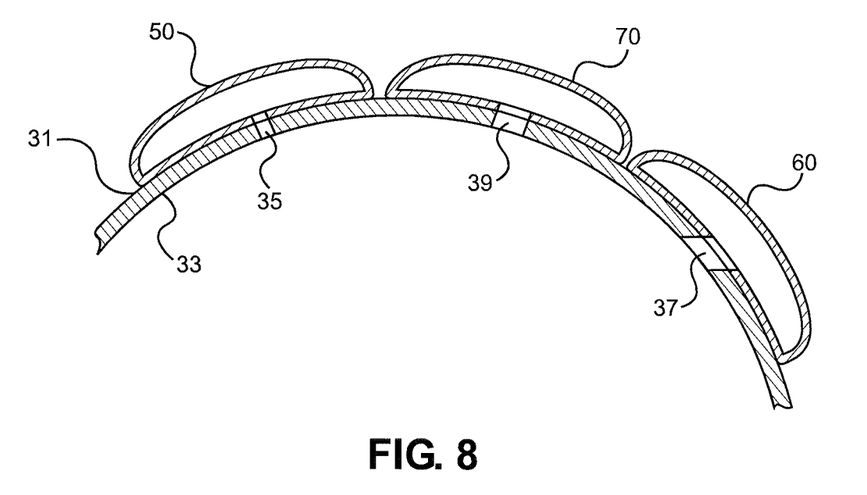
FIG. 8 is a close-up cross-sectional view of the sidewall of the urine lumen of the self-washing catheter showing the macro wash port at an angle with respect to the side wall of the urine lumen in order to facilitate a vortical flow within the interior of the urine lumen.

Turning to FIG. 8, the macro wash ports 37 may be configured at an angle with respect to the sidewall of the urine lumen 30 so as to facilitate the creation of a vortical flow of the wash solution within the interior of the urine lumen 30. The vortical flow, or whirlpool, resulting from the angled macro wash ports 37 creates a strong shear force near the bottom of a biofilm present on the interior surface 33 of the urine lumen 30. The ability to direct the strong shear force near the bottom of a biofilm (as opposed to the top of the biofilm) enables the wash solution to act directly on the bottom layer of the biofilm which is responsible for the bond to the interior surface 33 of the urine lumen 30. In contrast, a simple washout of the urine lumen 30 acting on the top layer of the biofilm will unlikely be able to reach the bottom bonded layer of the biofilm, greatly reducing the probability that the biofilm will be dislodged from the interior surface 33. In addition, the resulting vortical flow (or whirl pool) of the wash solution within the urine lumen 30 acts to further agitate the layers of the biofilm further increasing the likelihood that the biofilm will be dislodged from the interior surface 33 of the urine lumen 30. In contrast, the auxiliary lumen 70 is shown with an auxiliary macro port 39 which is positioned perpendicularly through the exterior surface 31 and interior surface 33 of the urine lumen 30.

Figure 9:
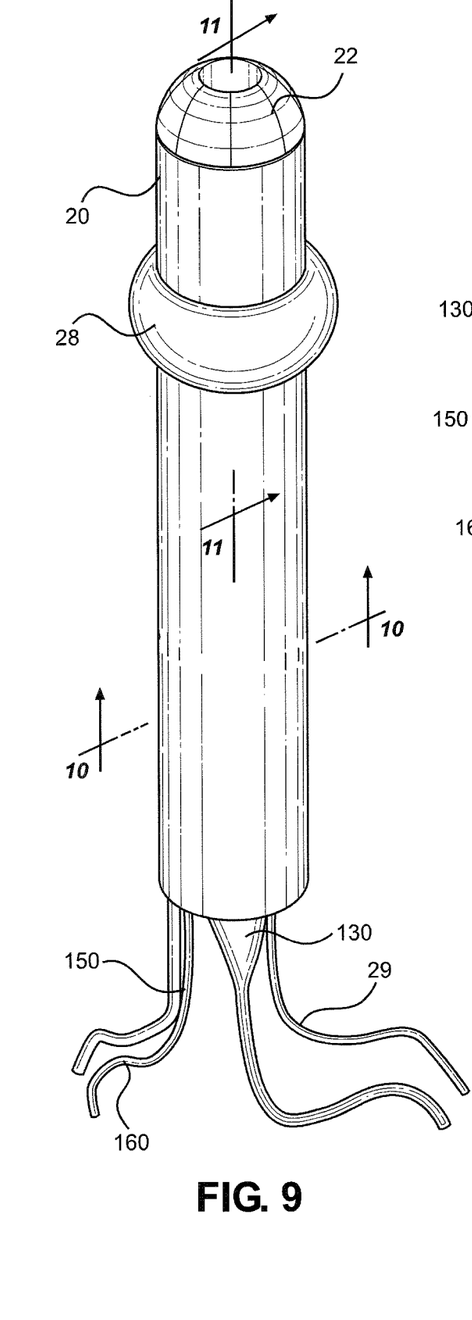
FIG. 9 is an isometric view of an alternative embodiment of the self-washing catheter equipped with a two-valve urine lumen closure device.

Turning to FIGS. 9 through 12, an alternative embodiment of an alternative embodiment of the self-cleaning catheter 10 is shown. In FIG. 9, the self-cleaning catheter 100 is shown with a hollow body 20 with a with an insertion tip 22 opposite an open end 24. The self-cleaning catheter 100 has a catheter opening 26 formed near the insertion tip 22.

Figure 10:
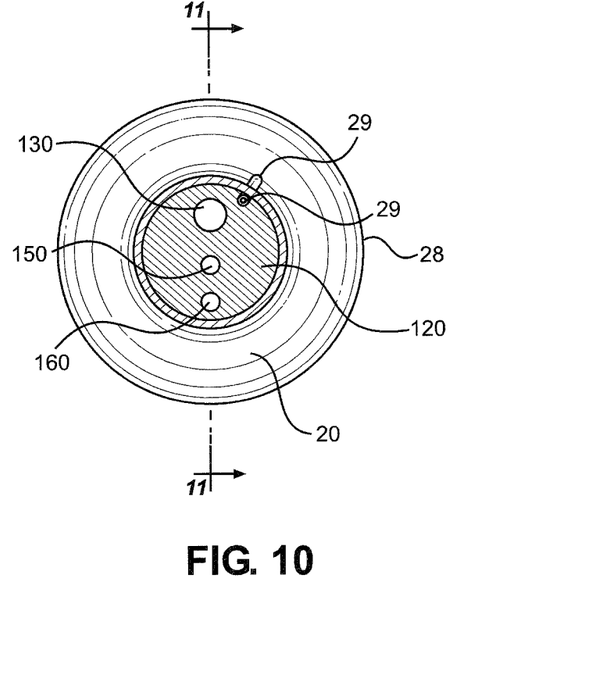
FIG. 10 is a cross-sectional view of the self-washing catheter along the lines 10-10 shown in FIG. 9 and showing an antimicrobial lumen, wash lumen and urine lumen open to and terminating at a lower seal.

The self-cleaning catheter 10 has a urine lumen 130, an antimicrobial lumen 150, and a wash lumen 160 all terminating in an open and at lower seal 120. It is preferred that the urine lumen 130, antimicrobial lumen 150, and wash lumen 160 and lower seal 120 are formed with a medical-grade silicone material and made by way of a silicone extrusion process. As a result, the lower seal 120 extends along the length of the lumens 130, 150 and 160 and is sealed against the inner surface of the outer shell 20.

Figure 11:
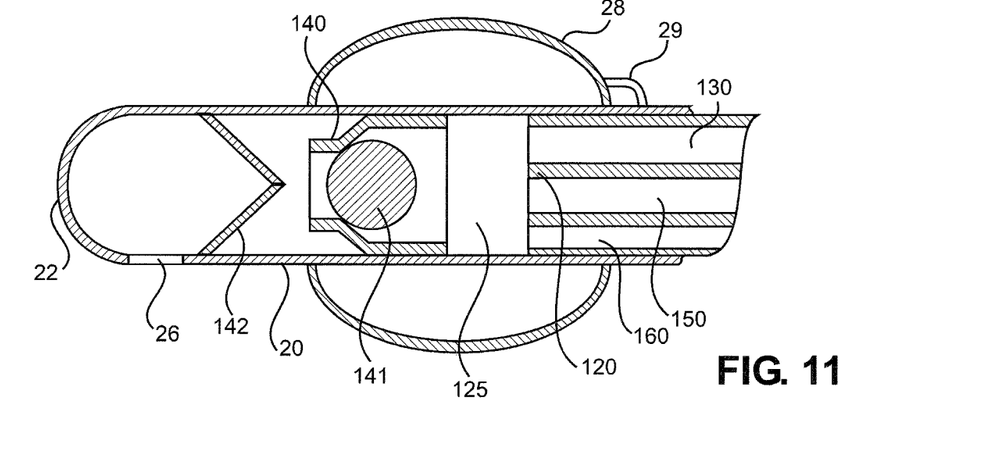
FIG. 11 is a cross-sectional view of the self-washing catheter along the lines 11-11 shown in FIG. 9 and showing a mixing chamber formed between the lower seal and a ball valve along with a secondary slit valve.
Figure 12:
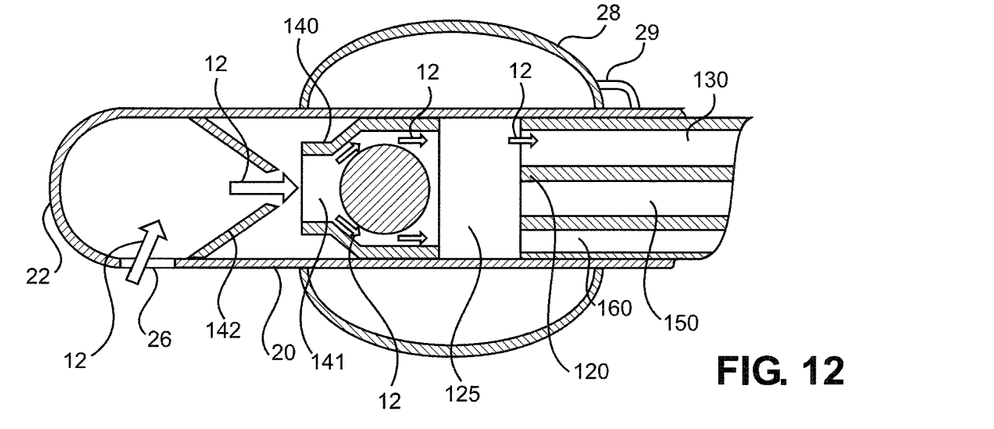
FIG. 12 is a cross-sectional view of the self-washing catheter along the lines 11-11 shown in FIG. 9 and showing, the ball valve and slit valve both in the open position allowing urine to pass into the mixing chamber and into the urine lumen.
Figure 13:
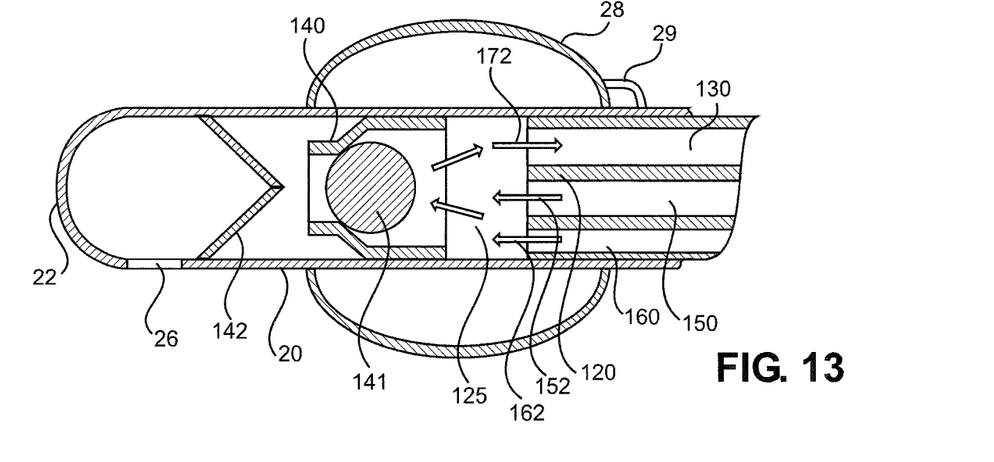
FIG. 13 is a cross-sectional view of the self-washing catheter along the lines 11-11 shown in FIG. 9 and showing the ball valve and secondary slit valve in the closed position and an antimicrobial agent and a wash composition each being introduced into the mixing chamber and into the urine lumen and wash and sterilize the same.

Turning to FIGS. 11 through 13, a mixing chamber 125 is formed between one-way main valve 140 and the lower seal 120. The urine lumen 130, antimicrobial lumen 150, and wash lumen 160 are open to and in fluid communication with the mixing chamber 125. Positioned between the catheter opening 26 and the one-way main valve 140 is secondary one-way valve 142. The one-way main valve 140 is shown as a ball valve and the secondary one-way valve 142 is shown as a one-way silicone slit valve. The one-way main valve 140 acts to prevent the flow of materials including waste materials such as urine and biofilm particulates, antimicrobial agents, and wash solutions from passing through the catheter opening 26 into the bladder of a user. The second one-way valve 142 is redundant to the one-way main valve 140 and is utilized to further reduce the risk of waste materials passing into the bladder from the catheter 100.

FIG. 12 shows waste material entering the catheter opening 26, passing through the second one-way valve 142 and the one-way main valve 140 (shown as ball valve 141) into the mixing chamber 125. A predetermined internal pressure is applied within the antimicrobial lumen 150 and wash lumen 160 to preclude the flow of urine into either the antimicrobial lumen 150 and wash lumen 160. The predetermined internal pressure may be created through a pressure reservoir 54 and a wash reservoir 64 connected to the antimicrobial lumen 150 and wash lumen 160. Such connections were shown in FIGS. 1 and 6 above and are omitted from the close-up views depicted in FIGS. 11-13.

As a result of the predetermined internal pressure created through the pressure reservoir 54 and wash reservoir 64, urine 12 is directed from the mixing chamber 125 to the inlet of the urine lumen 130 where it is then directed to and deposited in a urine storage reservoir 14, such as a collection bag or urine storage container.

FIG. 13 shows an antimicrobial solution 152 entering the mixing chamber 125 from the antimicrobial lumen 150 and a wash solution 162 entered the mixing chamber 125 from the wash lumen 160. The antimicrobial solution 152 and wash solution 162 mix in the mixing chamber 125 to form an antimicrobial wash solution mix 172. The mixing chamber 125 is pressurized by pressure reservoir 54, which drives the antimicrobial wash solution mix 172 through the urine lumen 130 at a sufficient flow rate to dislodge any biofilm growth within the urine lumen 130. In addition, the resulting antimicrobial wash solution mix 172 and pressure close the one-way main valve 140. Any leakage of the antimicrobial wash solution mix 172 past the one-way main valve 140 is barred from entering the bladder of the user by the second one-way valve 142. The two valves 140 and 142 cooperate together to ensure that no antimicrobial solution 152, wash solution 162, or antimicrobial wash solution mix 172 enter the bladder of the patient during use.

As a result of the various embodiments set forth above, the self-washing catheter 10 may be injected with various combinations of antimicrobial solutions 152 and wash solutions 162 in predetermined cycles and durations while the catheter 10 remains inserted within the patient.

Figure 14:
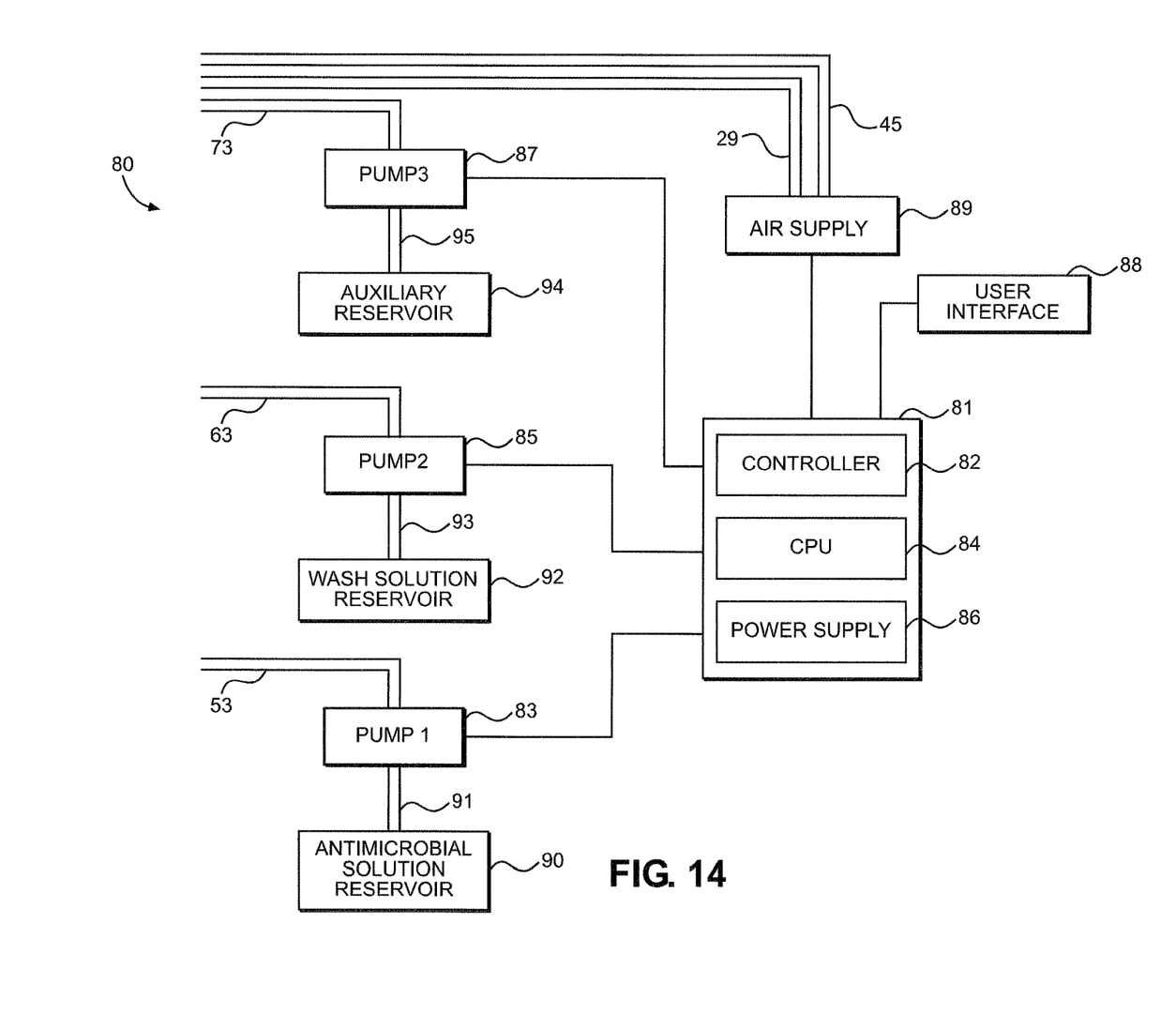
FIG. 14 is a schematic diagram of an automation system for controlling and automating the self-cleaning functionality of the self-cleaning catheter.

Turning to FIG. 14, an automated system 80 is shown with a controller 82, CPU 84 and a power supply 86 housed within a housing 81. The interconnections between the controller 82, CPU 84 and power supply 86 are omitted from view for brevity. The controller 82, CPU 84 and power supply 86 also control a manifold air supply 89. The anchor balloon fill port 29 and the closure balloon fill port 45 are independently inflatable by way of a manifold structure within the manifold air supply 89, the branches of which are independently controllable through electronically actuated valves. The automated system 80 also includes a user interface 88 to allow for programming and monitoring of the automated system 80.

Pump 1 83, pump 2 85, and pump 3 87 are each electrically connected to the controller 82, CPU 84 and power supply 86 and are powered and controlled by the same. Pump 1 83 is in fluid communication with an antimicrobial solution reservoir 90 which stores an antimicrobial agent. Pump 1 83 then draws the antimicrobial agent from the antimicrobial solution reservoir 90 and directs the same to the antimicrobial connection line 53 of the self-cleaning catheter 10.

Pump 2 85 is in fluid communication with a wash solution reservoir 92 which stores a wash solution. Pump 2 85 then draws the wash solution from the wash solution reservoir 92 and directs the same to the wash connection line 63 of the self-cleaning catheter 10.

Pump 3 87 is in fluid communication with an auxiliary reservoir 94 which stores an antimicrobial agent or a wash solution. Pump 3 87 then draws the stored agent or solution from the auxiliary reservoir 94 and directs the same to the auxiliary connection line 73 of the self-cleaning catheter 10. Alternatively, Pump 3 87 and the auxiliary reservoir 94 could be omitted with the auxiliary connection line 73 being connected to the manifold air supply 89.

While there have been shown what are presently considered to be preferred embodiments of the present invention, it will be apparent to those skilled in the art that various changes and modifications can be made herein without departing from the scope and spirit of the invention. Therefore, the spirit and scope of the appended claims should not be limited to the description of the preferred versions contained herein.

We claim:
1. A catheter comprising:
an outer shell with an insertion tip opposite an open end and a catheter opening formed near the insertion tip;
an anchor balloon affixed to the outer shell connected to an anchor fill port disposed within the outer shell;
a urine lumen in fluid communication with the catheter opening;
a urine lumen closure device located near the catheter opening within the outer shell and which when closed precludes a flow of a waste material from the urine lumen to the bladder of a patient;
an antimicrobial lumen disposed within the outer shell and in fluid communication with the urine lumen and terminating in an antimicrobial, connection port adjacent the open end of the outer shell, wherein the antimicrobial lumen is adjacent to the urine lumen and opens to the urine lumen at one or more micro ports;
a wash lumen disposed within the outer shell and in fluid communication with the urine lumen and terminating in a wash lumen port adjacent the open end of the outer shell, wherein the wash lumen is adjacent to the urine lumen and opens to the urine lumen at one or more macro wash ports; and
wherein the macro wash ports are configured o create a vortical flow of a wash solution within the interior of the urine lumen.
2. The catheter of claim 1 wherein the antimicrobial lumen is connected to an antimicrobial solution reservoir and an antimicrobial pump wherein an antimicrobial agent is stored within the antimicrobial solution reservoir and is delivered at a desired antimicrobial flow rate to the urine lumen.
3. The catheter of claim 1 wherein the urine lumen closure device is a closure balloon that encircles the urine lumen near the insertion tip.
4. The catheter of claim 1 wherein the urine lumen closure device is a one-way valve.
5. The catheter of claim 1 wherein the wash lumen is connected to a wash solution reservoir and wash solution pump wherein a wash composition is stored within the wash solution reservoir and is delivered in a desired wash flow rate to the urine lumen.

6. The catheter of claim 1 wherein the urine lumine closure device is a closure balloon that encircles the urine lumen near the insertion tip.

7. The catheter of claim 1 wherein the urine lumine closure device is a one-way valve.

8. A catheter comprising:
   an outer shell with an insertion tip opposite and open end and a catheter opening formed near the insertion tip;
   an anchor balloon affixed to the outer shell;
   a urine lumen in fluid communication with the catheter opening;
   an antimicrobial lumen disposed within the outer shell and in fluid communication with the urine lumen and terminating in an antimicrobial connection port adjacent the open end of the outer shell;
   a wash lumen disposed within the outer shell and in fluid, communication with the urine lumen and terminating in a wash lumen port adjacent the open end of the outer shell; and
   wherein the wash lumen port is configured to create a vortical low of a wash solution within the interior of the urine lumen.

9. The catheter of claim 8 further comprising an auxiliary lumen disposed within the outer shell and in fluid communication with the urine lumen and terminating in an auxiliary lumen connection port adjacent the open end of the outer shell.

10. The catheter of claim 9, wherein the auxiliary lumen is a antimicrobial lumen.

11. The catheter of claim 9, wherein the auxiliary lumen is a wash lumen.

12. The catheter of claim 9, wherein the auxiliary lumen further comprises macro ports.

* * * * *